US010603015B2

(12) United States Patent
Choi et al.

(10) Patent No.: US 10,603,015 B2
(45) Date of Patent: Mar. 31, 2020

(54) ULTRASONIC APPARATUS AND METHOD FOR CONTROLLING THE SAME

(71) Applicant: SAMSUNG ELECTRONICS CO., LTD., Suwon-si, Gyeonggi-do (KR)

(72) Inventors: Jae Young Choi, Uiwang-si (KR); Ki Won Sohn, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 618 days.

(21) Appl. No.: 14/844,505

(22) Filed: Sep. 3, 2015

(65) Prior Publication Data

US 2016/0066889 A1    Mar. 10, 2016

(30) Foreign Application Priority Data

Sep. 5, 2014    (KR) .................. 10-2014-0118852

(51) Int. Cl.
*A61B 8/14* (2006.01)
*A61B 8/08* (2006.01)
*A61B 6/00* (2006.01)
*A61B 8/00* (2006.01)
*A61B 6/12* (2006.01)

(52) U.S. Cl.
CPC .......... *A61B 8/5207* (2013.01); *A61B 6/5247* (2013.01); *A61B 8/085* (2013.01); *A61B 8/5261* (2013.01); *A61B 6/12* (2013.01); *A61B 6/5294* (2013.01); *A61B 8/0841* (2013.01); *A61B 8/4405* (2013.01); *A61B 8/464* (2013.01); *A61B 8/5292* (2013.01)

(58) Field of Classification Search
CPC ....... A61B 6/12; A61B 6/5247; A61B 6/5294; A61B 8/0841; A61B 8/085; A61B 8/4405; A61B 8/464; A61B 8/5207; A61B 8/5261; A61B 8/5292
See application file for complete search history.

(56) References Cited

U.S. PATENT DOCUMENTS

| 5,662,109 A | 9/1997 | Hutson |
| 5,664,573 A | 9/1997 | Shmulewitz |

(Continued)

FOREIGN PATENT DOCUMENTS

| JP | 2008-513090 | 5/2008 |
| KR | 10-2008-0034664 | 4/2008 |

(Continued)

OTHER PUBLICATIONS

Korean Notice of Allowance dated May 31, 2016 in corresponding Korean Patent Application No. 10-2014-00118852.

(Continued)

*Primary Examiner* — Mark D Remaly
(74) *Attorney, Agent, or Firm* — Staas & Halsey LLP

(57) ABSTRACT

An ultrasonic apparatus and method for controlling the same, by which whether a biopsy is required is determined based on X-ray and ultrasound images. An ultrasonic apparatus includes an image processing unit for matching or correlating an area of interest in an ultrasound image of a subject and an area of interest in a X-ray image of the subject; a controller for analyzing the matched or matching area of interest and determining whether a biopsy is required for the subject; and a display for displaying the determination as to whether the biopsy is required.

8 Claims, 19 Drawing Sheets

(56) References Cited

U.S. PATENT DOCUMENTS

| | | | | |
|---|---|---|---|---|
| 2003/0007598 | A1* | 1/2003 | Wang | A61B 6/463 |
| | | | | 378/37 |
| 2004/0068170 | A1 | 4/2004 | Wang et al. | |
| 2005/0059894 | A1* | 3/2005 | Zeng | A61B 1/00055 |
| | | | | 600/476 |
| 2008/0084961 | A1* | 4/2008 | Keppel | A61B 6/0414 |
| | | | | 378/37 |

FOREIGN PATENT DOCUMENTS

| | | |
|---|---|---|
| KR | 10-2008-0070767 | 7/2008 |
| KR | 10-0971417 | 7/2010 |

OTHER PUBLICATIONS

Korean Office Action dated Nov. 16, 2015 in corresponding Korean Patent Application No. 10-2014-0118852.

\* cited by examiner

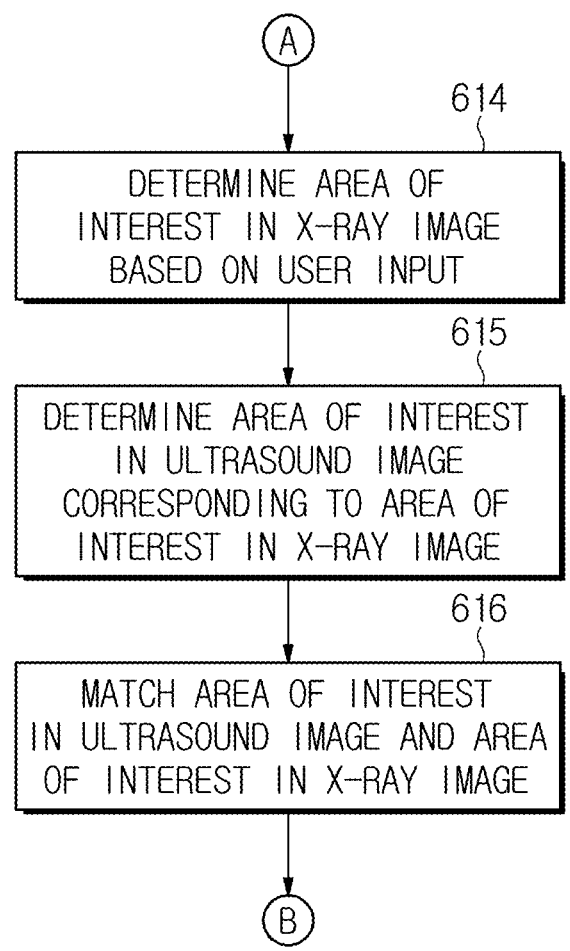

ULTRASONIC APPARATUS AND METHOD FOR CONTROLLING THE SAME

CROSS-REFERENCE TO RELATED APPLICATION(S)

This application claims the benefit under 35 U.S.C. § 119(a) of a Korean patent application filed on Sep. 5, 2014 in the Korean Intellectual Property Office and assigned Serial No. 10-2014-0118852, the entire disclosure of which is incorporated hereby incorporated by reference.

BACKGROUND

1. Field

The present disclosure relates to an ultrasonic apparatus that irradiates ultrasound to a subject and generates an ultrasound image and a method for controlling the ultrasonic apparatus.

2. Description of the Related Art

Compared to other diagnostic imaging apparatuses, such as X-ray diagnostic apparatuses, X-ray Computerized Tomography (CT) scanners, Magnetic Resonance Imaging (MRI) apparatuses, nuclear medicine diagnostic apparatuses, etc., ultrasonic apparatuses have many advantages that they are compact, inexpensive, able to display in real time, and safe because of no exposure to radiation, and are thus widely used for diagnosis in cardiology clinics, abdominal pain clinics, urology clinics, and women clinics.

If a patient is suspected to have a tumor as a result of an ultrasonic diagnosis, a biopsy may be performed on the body portion suspected to have the tumor for a more accurate diagnosis. The biopsy may be performed using a needle to be inserted into the inside of the patient to take tissue.

Meanwhile, due to the needle insertion to take tissue, the biopsy may cause mental and physical pains to the patient. Therefore, there is a need to closely review whether a biopsy is required before performing the biopsy.

SUMMARY

The present disclosure provides an ultrasonic apparatus and method for controlling the same, by which whether a biopsy is required is determined based on X-ray and ultrasound images.

In accordance with an aspect of the present disclosure, an ultrasonic apparatus includes an image processing unit for matching an area of interest in an ultrasound image of a subject and an area of interest in a X-ray image of the subject; a controller for analyzing the matched or matching area of interest and determining whether a biopsy is required for the subject; and a display for displaying the determination as to whether the biopsy is required.

The controller may determine whether the biopsy is required for the subject by comparing characteristic information of the matched area of interest with predetermined reference characteristic information.

The characteristic information of the matched area of interest may include at least one of the size, shape, texture, spiculation form, and brightness per unit area of the area of interest.

The controller may determine whether the biopsy is required for the subject by using the comparison result and a subject parameter.

The subject parameter may include at least one of tissue density, Body Mass Index (BMI), the number of biopsies, information about family history of illness, and a particular gene of the subject.

The controller may update the reference characteristic information based on the determination of whether the biopsy is required.

The controller may obtain at least one of a true positive rate and a false positive rate by analyzing the matched area of interest in order to determine whether the biopsy is required for the subject.

The controller may determine whether the biopsy is required for the subject by comparing at least one of the obtained true positive rate and false positive rate with at least one of predetermined reference true positive rate and reference false positive rate.

The controller may determine reference true positive rate and reference false positive rate based on predetermined reference characteristic information.

The display may display diagnosis guidelines based on the determination of whether the biopsy is required.

The display may display a biopsy recommendation screen if the controller determines that the biopsy is required, and display an alternative diagnosis method recommendation screen if the controller determines that the biopsy is not required.

The image processing unit may match an area of interest in the ultrasound image determined based on a user input and an area of interest in the X-ray image determined based on the area of interest in the ultrasound image.

In accordance with another aspect of the present disclosure, a method for controlling an ultrasonic apparatus includes matching an area of interest in an ultrasound image of a subject and an area of interest in a X-ray image of the subject; analyzing the matched area of interest and determining whether a biopsy is required for the subject; and displaying the determination of whether the biopsy is required.

Determining whether a biopsy is required may include determining whether the biopsy is required for the subject by comparing characteristic information of the matched area of interest with predetermined reference characteristic information.

The characteristic information of the matched area of interest may include at least one of the size, shape, texture, spiculation form, and brightness per unit area of the area of interest.

Determining whether a biopsy is required may include determining whether the biopsy is required for the subject by using the comparison result and a subject parameter.

The subject parameter may include at least one of tissue density, Body Mass Index (BMI), the number of biopsies, information about family history of illness, and a particular gene of the subject.

The method may further include updating the reference characteristic information based on the determination of whether the biopsy is required.

Determining whether a biopsy is required may include obtaining at least one of a true positive rate and a false positive rate by analyzing the matched area of interest in order to determine whether the biopsy is required for the subject.

Determining whether a biopsy is required may include determining whether the biopsy is required for the subject by comparing at least one of the obtained true positive rate and false positive rate with at least one of predetermined reference true positive rate and reference false positive rate.

Determining whether a biopsy is required may include determining reference true positive rate and reference false positive rate based on predetermined reference characteristic information.

Displaying the determination of whether the biopsy is required may include displaying diagnosis guidelines based on the determination of whether the biopsy is required.

Displaying diagnosis guidelines may include displaying a biopsy recommendation screen if it is determined that the biopsy is required, and displaying an alternative diagnosis method recommendation screen if it is determined that the biopsy is not required.

The method may further include: determining an area of interest in the ultrasound image based on a user input; and determining an area of interest in an X-ray image based on the area of interest in the ultrasound image.

In accordance with a further aspect of the present disclosure, a method includes correlating an area of interest of an ultrasound image with an X-ray image designating correlated ultra sound and X-ray images in the area of interest using displayed ultrasound and X-ray images, determining whether a biopsy is required from characteristics of the area of interest of the correlated ultra sound and X-ray images and indicating whether a biopsy is required.

The designating of the area of interest in the ultrasound image may be performed by a user.

The determining may compare the characteristics of the area of interest with reference characteristics.

The reference characteristics may include an average of image characteristics of a sample group where a biopsy has been performed and the determining compares the characteristics of the area of interest with the average of image characteristics.

The characteristics of the area of interest and the reference characteristics may be image characteristics.

The area of interest of the ultrasound image and the X-ray image may be correlated by a user designating an ultrasound image area and designating a corresponding X-ray image area.

The indicating may display, when a biopsy is required, a biopsy required confidence measure, a risk of false positive measure and one of a biopsy recommendation and a biopsy guideline and displays, when a biopsy is not required, the biopsy required confidence measure, the risk of false positive measure and an alternative diagnosis recommendation.

In accordance with another aspect of the present disclosure a non-transitory computer readable medium storing an ultrasonic apparatus method may include a method that includes correlating an area of interest of an ultrasound image with an X-ray image by designating correlated ultra sound and X-ray images in the area of interest using displayed ultrasound and X-ray images, determining whether a biopsy is required from characteristics of the area of interest of the correlated ultra sound and X-ray images, and indicating whether a biopsy is required.

In accordance with a still further aspect of the present disclosure, a method includes designating correlated areas of interest in an ultrasound image and an X-ray image using displayed ultrasound and X-ray images, determining whether a biopsy is required from characteristics of the correlated areas of interest of the ultra sound and X-ray images and indicating whether a biopsy is required.

Other aspects, advantages, and salient features of the disclosure will become apparent to those skilled in the art from the following detailed description, which, taken in conjunction with the annexed drawings, discloses exemplary embodiments of the disclosure

BRIEF DESCRIPTION OF THE DRAWINGS

The above and other features and advantages of the present disclosure will become more apparent by describing in detail exemplary embodiments thereof with reference to the attached drawings in which:

FIGS. 9A to 9C are flowcharts illustrating a method for controlling an ultrasonic apparatus to match areas of interest, according to various embodiments of the present disclosure;

Throughout the drawings, like reference numerals will be understood to refer to like parts, components, and structures.

DETAILED DESCRIPTION

Figure 1:
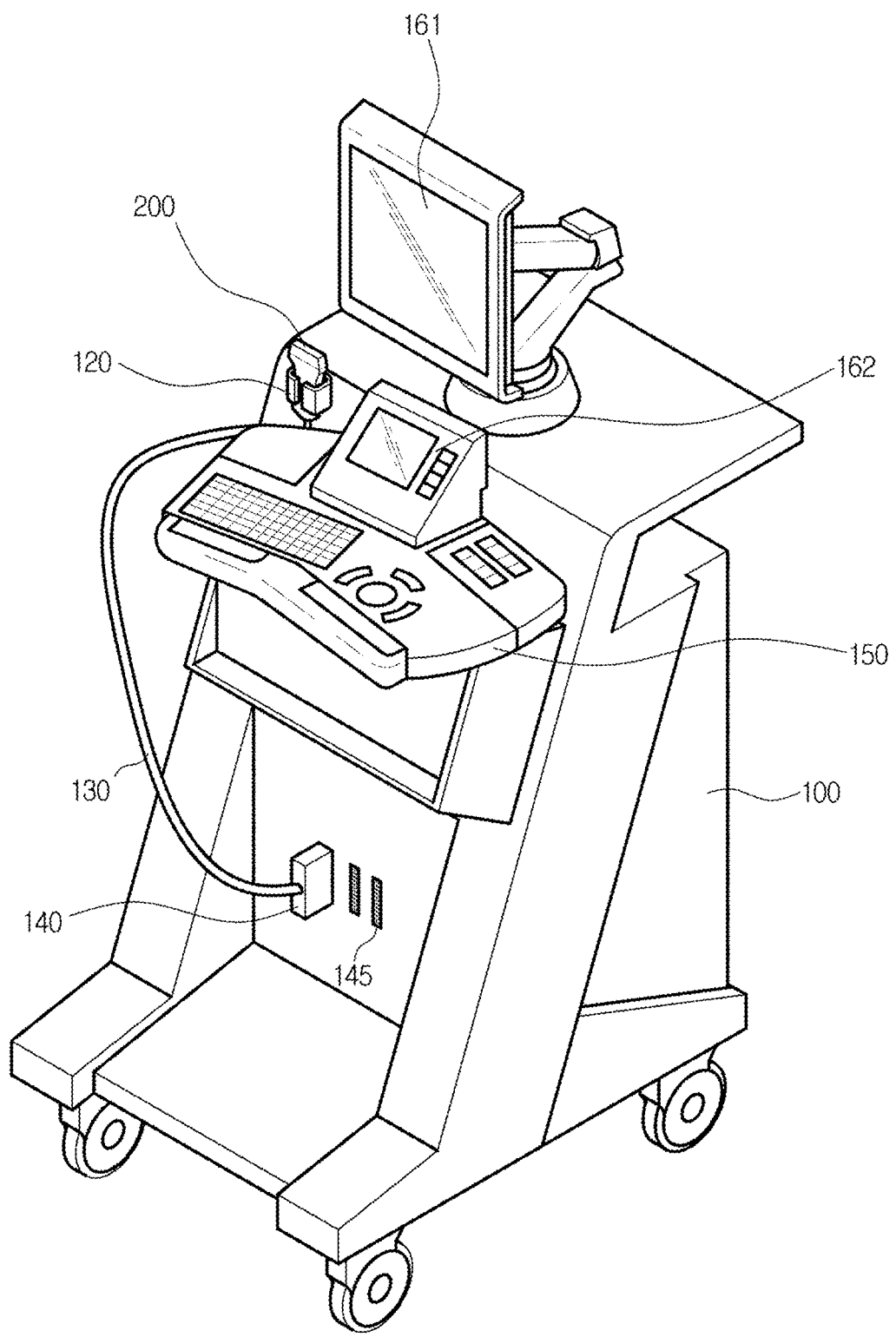
FIG. 1 is a perspective view of an embodiment of an ultrasonic apparatus.

The present disclosure will now be described more fully with reference to the accompanying drawings, in which exemplary embodiments of the disclosure are shown. The disclosure may, however, be embodied in many different forms and should not be construed as being limited to the embodiments set forth herein; rather, these embodiments are provided so that this disclosure will be thorough and complete, and will fully convey the concept of the disclosure to those skilled in the art. Like reference numerals in the drawings denote like elements, and thus their description will be omitted. In the description of the present disclosure, if it is determined that a detailed description of commonly-used technologies or structures related to the embodiments of the present disclosure may unnecessarily obscure the subject matter of the invention, the detailed description will be omitted. It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section.

Embodiments of an ultrasonic apparatus and method for controlling the same will now be described in detail with reference to accompanying drawings.

The term 'subject' as herein used may refer to a breast of a patient, but is not limited thereto. In addition, the term 'user' as herein used may refer to a doctor, but is not limited thereto.

FIG. 1 is a perspective view of an embodiment of an ultrasonic apparatus. Referring to FIG. 1, the ultrasonic apparatus may include a main unit 100, an ultrasonic probe 200, an input unit 150, and a display 160.

One or more female connectors 145 may be included in one side of the main unit 100. The female connector 145 may be mechanically combined with a male connector 140 coupled with a cable 130.

On the bottom side of the main unit 100, there may be multiple casters or rollers (not shown) for mobility of the ultrasonic apparatus. The multiple casters may fix the ultrasonic apparatus in a particular location, or may move the ultrasonic apparatus in a particular direction. Such an ultrasonic apparatus may be referred to as a cart type ultrasonic apparatus.

Alternatively, unlike what is shown in FIG. 1, the ultrasonic apparatus may be a portable ultrasonic apparatus that may be carried for long distance. In this case, the portable ultrasonic apparatus may not include any casters. For example, the portable apparatus may be a PACS viewer, smart phone, laptop computer, personal digital assistant (PDA), tablet personal computer (PC), etc., but is not limited thereto.

The ultrasonic probe 200 is a device to contact the body surface of a subject and may transmit and receive ultrasound. Specifically, the ultrasonic probe 200 serves to transmit ultrasound to the inside of the subject according to a signal provided from the main unit 100, and receive echo ultrasound reflected from a particular part of the subject and forward the ultrasound to the main body 100.

The ultrasonic probe 200 is connected to an end of the cable 130, the other end of which may be connected to a male connector 140. The male connector 140 connected to the other end of the cable 130 may be mechanically combined with the female connector 145 of the main unit 100.

Alternatively, a wireless connection may be used between the main body 100 and the ultrasonic probe 200. In this case, the ultrasonic probe 200 may wirelessly transmit echo ultrasounds reflected from the subject to the main body 100. In addition, multiple ultrasonic probes 200 may be connected to a single main body.

The ultrasonic probe 200 may be a one dimensional (1D) array probe or two dimensional (2D) array probe depending on the arrangement form of the transducer elements.

The main unit 100 may include an image processing unit 170 for converting the received echo ultrasounds to an ultrasound image. The image processing unit 170 may be implemented in hardware, such as a microprocessor, or in software that may be carried out in the hardware stored on a non-transitory computer readable storage medium.

The image processing unit 170 may generate an ultrasound image through a scan conversion process for the echo ultrasounds. Here, the ultrasound image may include a gray scale image obtained by scanning a subject in A mode (or amplitude mode), B mode (brightness mode), or M mode (or motion mode) or a Doppler image that represents a moving subject based on the Doppler effect. The Doppler image may include a bloodstream Doppler image (also referred to as a color Doppler image), a tissue Doppler image that represents movement of tissues, or a spectral Doppler image that represents the moving speed of the subject in a waveform.

The image processing unit 170 may extract B mode components from the echo ultrasounds received by the ultrasonic probe 200 to generate a B mode image. The image processing unit 170 may generate an ultrasound image in which the intensity of the echo ultrasounds appears to be bent based on the B mode components.

Similarly, the image processing unit 170 extracts Doppler components from the echo ultrasounds, and may generate a Doppler image that represents the movement of the subject in colors or waveforms based on the Doppler components.

In addition, the image processing unit 170 may generate a three dimensional (3D) ultrasound image through volume rendering of volume data obtained from the echo ultrasounds, and generate an elastographic image in which deformation degrees of a subject due to pressure are imaged. Furthermore, the image processing unit 170 may represent various additional information in text, graphics, etc., on the ultrasound image.

The ultrasound image may be stored in a storage unit 400 internal or external to the main unit 100. Alternatively, the ultrasound image may be stored in a Web storage or cloud server that has a storage function on the Web.

The input unit 150 may receive an instruction associated with an operation of the ultrasonic apparatus. For example, the input unit 150 may receive a mode selection instruction to select e.g., A mode, B mode, M mode, or Doppler image mode. Further, the input unit 150 may receive an instruction to start ultrasonic diagnosis.

The instruction input through the input unit 150 may be sent to the main unit 100 through wired or wireless communications.

The input unit 150 may include, for example, at least one of a keyboard, foot switch, and foot pedal. The keyboard may be implemented in hardware and located on the upper part of the main unit 100. The keyboard may include at least one of switches, keys, a joy stick, and a trackball. Alternatively, the keyboard may be implemented in software, such as a graphic user interface. In this case, the keyboard may be displayed through a sub display 161 or a main display 162. The foot switch or foot pedal may be placed in the bottom of the main unit 100, and the user may use the foot pedal to control operation of the ultrasonic apparatus.

The display 160 may include the main display 161 and the sub display 162.

The sub display 162 may be included in the main unit 100. In the embodiment of FIG. 1, the sub display 162 is shown to be located above the input unit 150. The sub display 162 may display an application related to operation of the ultrasonic apparatus. For example, the sub display 162 may display menus or instructions necessary for ultrasonic diagnosis. The sub display 162 may be implemented with e.g., a Cathode Ray Tube (CRT), a Liquid Crystal Display (LCD), etc.

The main display 161 may be included in the main unit 100. In the embodiment of FIG. 1, the sub display 161 is shown to be located above the sub display 162. The main display 161 may display ultrasound images obtained in the process of ultrasonic diagnosis in response to an input to the input unit 150. Similar to the sub display 162, the main display 161 may be implemented with a CRT or LCD. Although the embodiment of FIG. 1 shows that the main display 161 is incorporated in the main unit 100, the main display 161 may be implemented to be detachable from the main unit 100.

The embodiment of FIG. 1 shows that the main display 161 and the sub display 162 are both included in the ultrasonic apparatus, but in some other embodiments, the sub display 162 may be omitted. In the latter case, the application or menus, otherwise displayed through the sub display 162, may be displayed through the main display.

The ultrasonic apparatus may further include a communication unit. The communication unit is connected to a network 500 wiredly or wirelessly to communicate with an external device or server. The communication unit may exchange data with a hospital server or another medical equipment in the hospital through the Picture Archiving and Communication System (PACS). Furthermore, the communication unit may communicate data according to the Digital Imaging and Communications in Medicine (DICOM) standard.

The communication unit may transmit or receive data related to diagnosis of the subject, such as an ultrasound image, echo ultrasound, Doppler data, etc. of the subject, and also a medical image captured by the other medical equipment, such as Computerized Tomography (CT), Magnetic Resonance Imaging (MRI) and X-ray equipment. Further, the communication unit may receive information regarding the patient's diagnosis history or treatment schedule, and use the information in the diagnosis of the subject. The communication unit may perform data communication not only with a server or medical equipment in the hospital but also with portable terminals of doctors or patients.

The communication unit may be connected to the network 500 wired or wirelessly to exchange data with a server, medical equipment, or portable terminal. The communication unit may include one or more components that enable communication with an external device, such as a short-range communication module, cable communication module, and mobile communication module.

The short-range communication module refers to a module for near distance communication within a predetermined range. For example, the short-range communication module may include Wireless Local Area Network (WLAN), Wi-Fi, Bluetooth, Zigbee, Wi-Fi Direct (WFD), Ultra Wideband (UWB), Infrared Data Association (IrDA), Bluetooth Low Energy (BLE), Near Field Communication (NFC), etc., but is not limited thereto.

The cable communication module refers to a module for communication using electrical or optical signals, including, for example, a pair cable, a coaxial cable, on optical fiber cable, an Ethernet cable, etc.

The mobile communication module transmits and receives RF signals to and from one of a base station, an external terminal, and a server in the mobile communication network. The RF signal may include a voice call signal, a video call signal or different types of data involved in transmission/reception of a text/multimedia message.

Figure 2A:
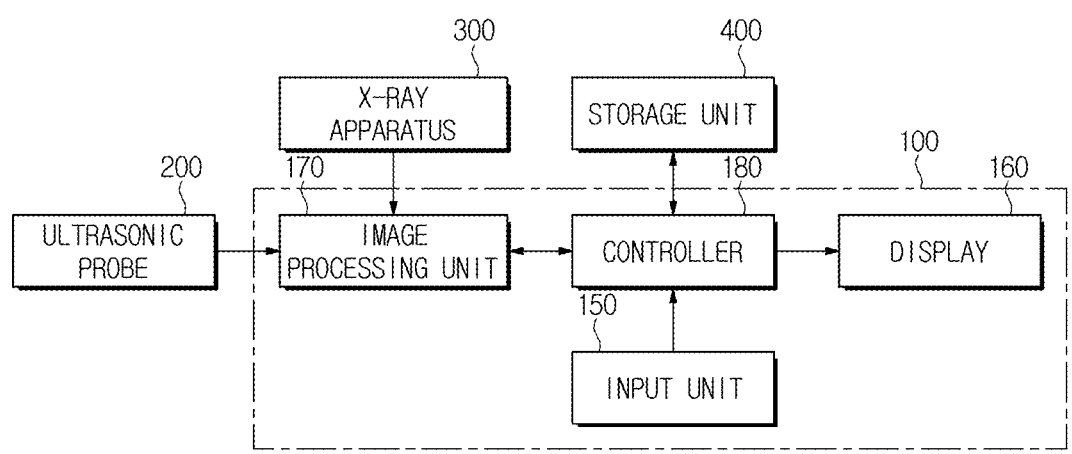
FIGS. 2A and 2B are control block diagrams of an ultrasonic apparatus, according to various embodiments of the present disclosure.
Figure 2B:
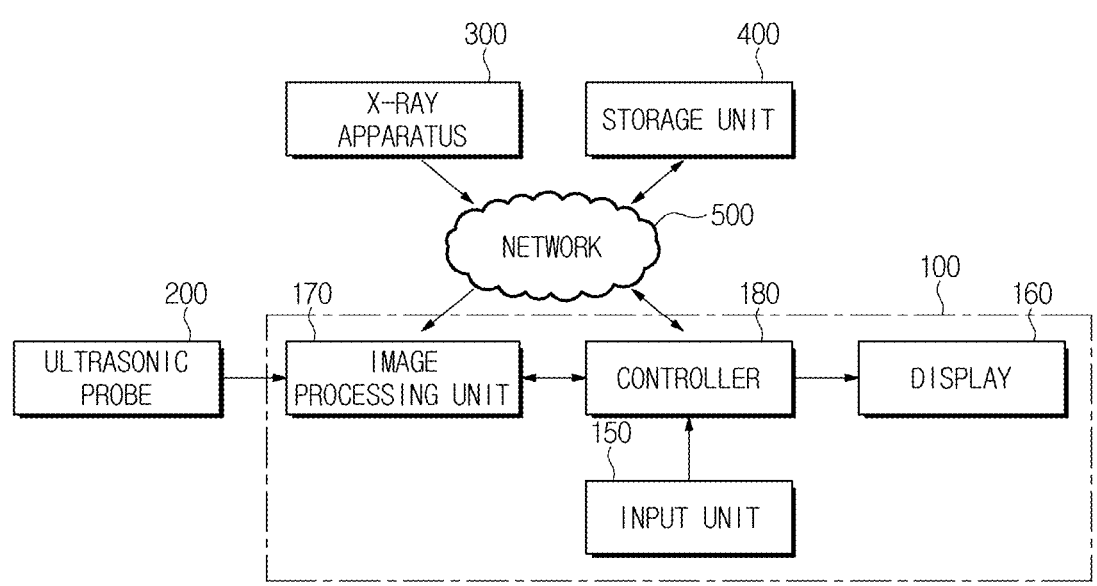

FIGS. 2A and 2B are control block diagrams of an ultrasonic apparatus, according to various embodiments of the present disclosure.

Referring to FIG. 2A, the ultrasonic apparatus in accordance with an embodiment of the present disclosure may include an ultrasonic probe 200 for irradiating ultrasound to a subject and receive corresponding echo ultrasound, an image processing unit 170 for matching an area of interest in an ultrasound image generated based on the echo ultrasound and an area of interest in an X-ray image delivered from an external X-ray apparatus 300, a controller 180 for analyzing the matched areas of interest and determining whether a biopsy of the subject is required, a display 160 for displaying the determination result, and an input unit 150 for receiving an instruction to designate an area of interest from the user. The apparatus may further include a storage unit for storing reference characteristics information for determination of whether the biopsy is required.

The ultrasonic probe 200 may include a plurality of transducer elements on its front, which irradiate ultrasound to the subject and receive echo ultrasounds reflected from the subject. The ultrasonic probe 200 may be classified by the arrangement form of its transducer elements.

Specifically, the ultrasonic probe 200 may include a convex array probe having transducer elements arranged along a curve to transmit or receive ultrasound or a linear array probe having transducer elements arranged in a straight line to transmit or receive ultrasounds. Furthermore, unlike the above example where the transducer elements are linearly arranged, the ultrasonic probe 200 may include a 2D array probe where the transducer elements are two dimensionally arrayed.

The ultrasonic probe 200 may irradiate ultrasounds to a subject and receive echo ultrasound having information regarding the subject, by means of the transducer elements. The echo ultrasound may be forwarded to the image processing unit 170.

The image processing unit 170 may then generate an ultrasound image based on the echo ultrasound. Since ultrasound differ in reflection/absorption degrees depending on the medium, the echo ultrasounds reflected from the subject may include information regarding the inside of the subject. Accordingly, the image processing unit 170 may generate the ultrasound image including the information regarding the inside of the subject based on the echo ultrasounds.

While the image processing unit 170 directly generates an ultrasound image in the embodiment of FIG. 2A, it may also be possible for the image processing unit 170 to receive the ultrasound image from the outside.

The image processing unit 170 may also receive an X-ray image from the external X-ray apparatus 300. Upon reception of the X-ray image, the image processing unit 170 may match an area of interest in the previously generated ultrasound image and an area of interest in the received X-ray image.

The term "area of interest" as used herein may refer to an area for which it is determined whether a biopsy is required and be defined to be an area to be determined in the ultrasound image or the X-ray image as well as a corresponding area in the subject.

For example, in a case the subject is a breast of a patient, the area of interest may refer to an area including breast lesions. However, this is merely an example and the area of interest may be freely defined as long as it is an area for which it is determined whether a biopsy is required.

The area of interest may be determined by a user input or internal operation of the apparatus. For example, the input unit 150 may receive an instruction to designate the area of interest from the user and forward the instruction to the controller 150. The controller 150 may then control the image processing unit 170 to determine the area of interest based on the user input.

Figure 3A:
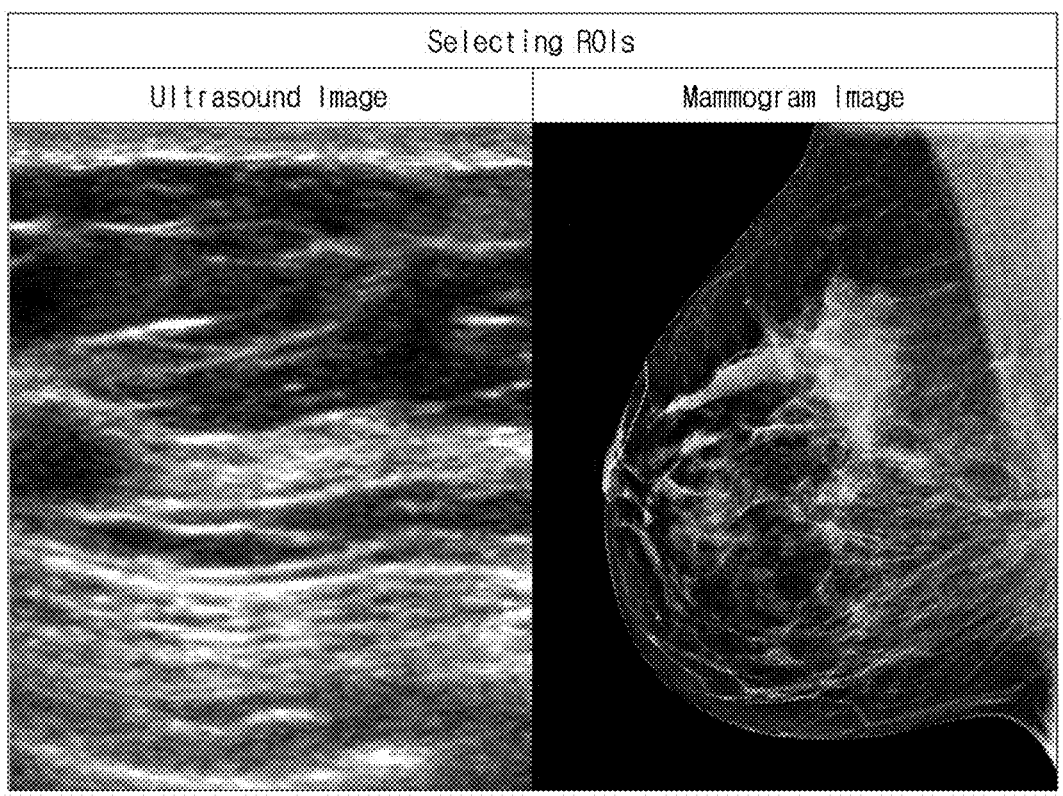
FIGS. 3A, 3B, and 3C show images for explaining how to designate an area of interest, according to an embodiment of the present disclosure.
Figure 3B:
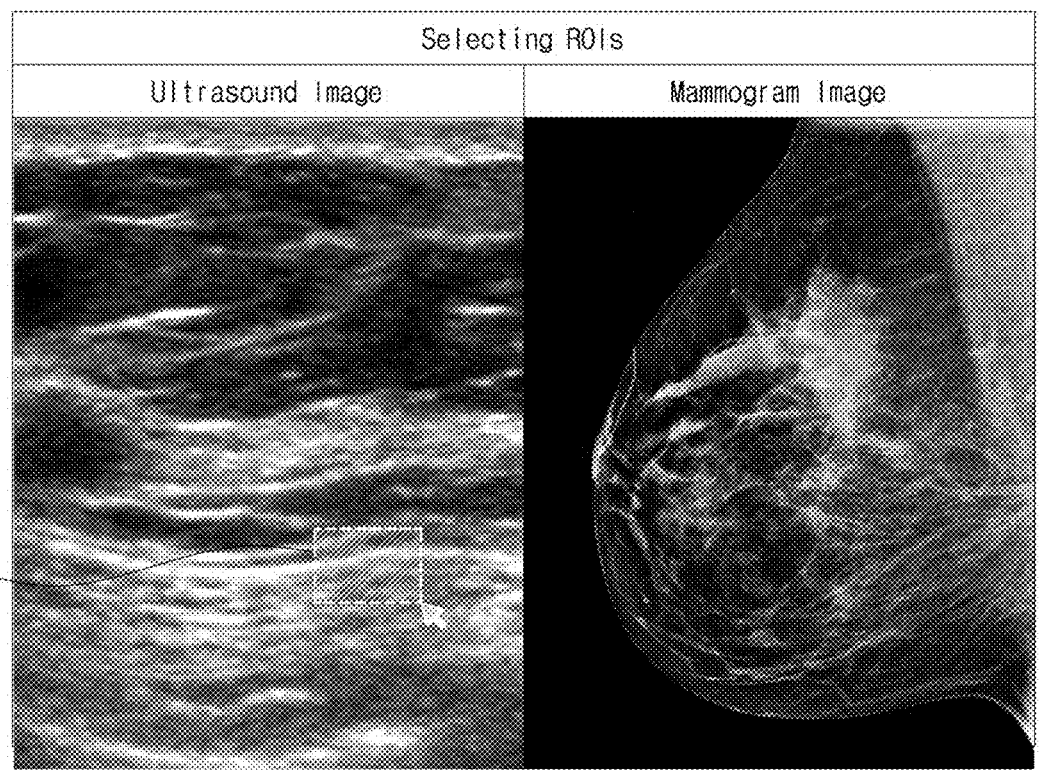
Figure 3C:
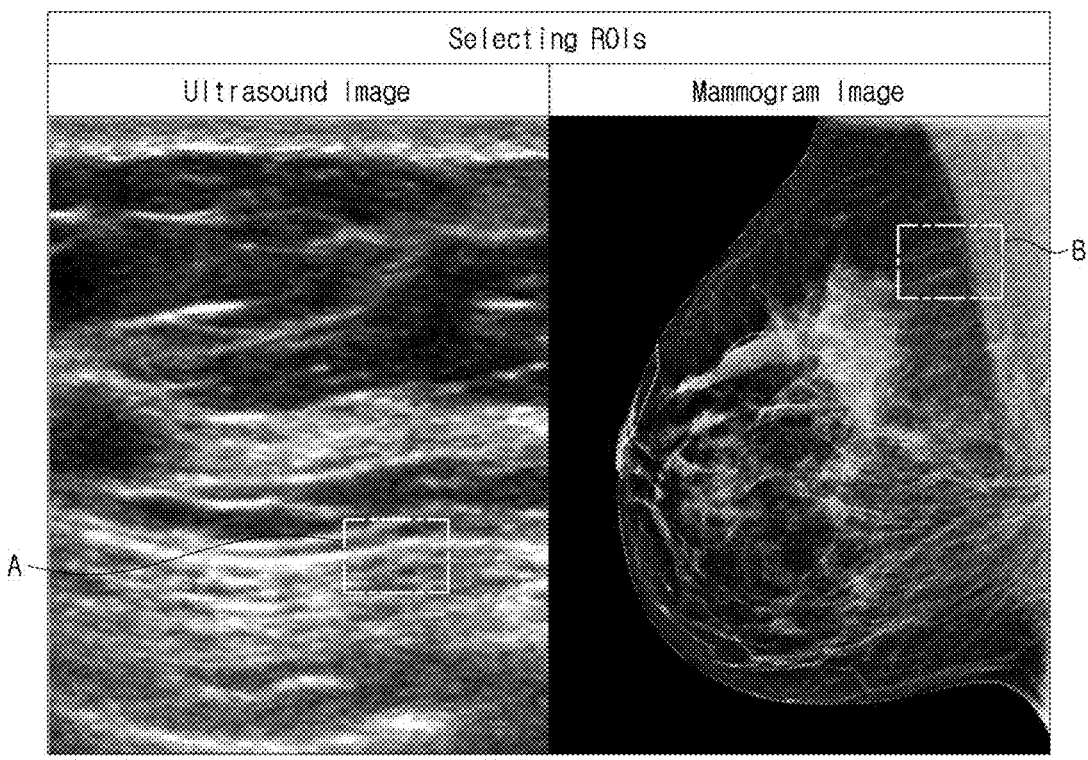

FIGS. 3A, 3B, and 3C show images for explaining how to designate an area of interest, according to an embodiment of the present disclosure.

The display 160 may display an image for designation of the area of interest. Specifically, at least one of ultrasound image and X-ray image of the subject may be displayed in the display 160. Referring to FIG. 3A, both of ultrasound and X-ray images of the subject are simultaneously displayed in the display 160.

The input unit 150 may receive an instruction to designate the area of interest from the user. Referring to FIG. 3B, the input unit 150 may receive an instruction from the user to designate area A in the ultrasound image as the area of interest.

The input unit 150 then forwards the instruction to the controller 180, and the image processing unit 170 may determine the area A in the ultrasonic area as the area of interest under control of the controller 180.

After determining the area of interest in the ultrasound image, the image processing unit 170 may determine a corresponding area in the X-ray image to be its area of interest. Here, the area of interest in the X-ray image corresponding to that of the ultrasound image may refer to an area in the X-ray image that displays a location of a part of the subject displayed in the area of interest in the ultrasound image (hereinafter, referred to as an area of interest in the subject).

Referring to FIG. 3C, the image processing unit 170 may determine area B in the X-ray image which corresponds to an area of interest in the ultrasound image, and the display 160 may indicate the Area B in the X-ray image. FIGS. 3A to 3C show images for explaining how to determine an area of interest in an ultrasound image in response to a user input and how the image processing unit 170 determines an area of interest in an X-ray image which corresponds to the area of interest in the ultrasound image. However, it is also possible to determine an area of interest in an X-ray image in response to a user input and then let the image processing unit 170 determine an area of interest in an ultrasound image which corresponds to the area of interest in the X-ray image. Moreover, it is also possible to determine both areas of interest in ultrasound and X-ray images in response to a user input.

Figure 4:
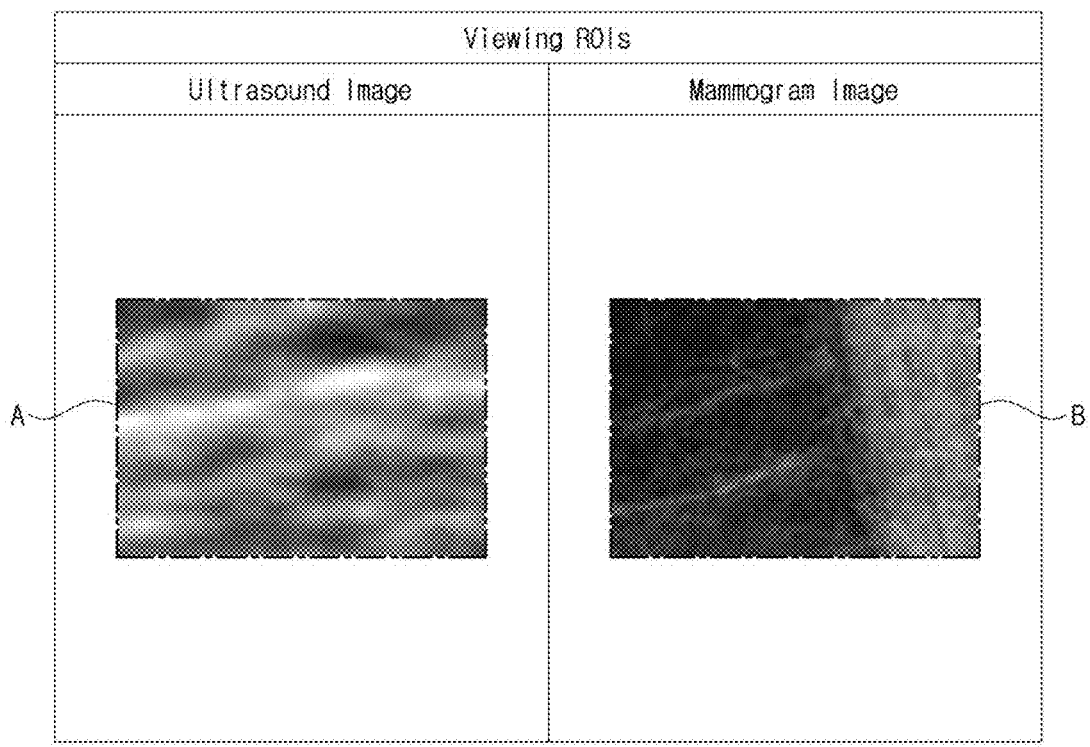
FIG. 4 shows an image for explaining how to indicate areas of interest in ultrasound and X-ray images, according to an embodiment of the present disclosure.

FIG. 4 shows an image for explaining how to indicate areas of interest in ultrasound and X-ray images, according to an embodiment of the present disclosure.

When the areas of interest in ultrasound and X-ray images have been determined, the display 160 may display the areas of interest in the ultrasound and X-ray images. By doing this, the ultrasonic apparatus may visually provide the user with the areas of interest set or designated in the ultrasound image and X-ray image.

After determining the areas of interest, the image processing unit 170 may match the area of interest in the ultrasound image and the area of interest in the X-ray image. Here, the matching or correlation may refer to a corresponding an area of interest in the ultrasound image and an area of interest in the X-ray image determined using coordinates of a coordinate system of the images. Through the matching, an area of interest in the subject may be checked out both in the X-ray and ultrasound images, thereby increasing accuracy of the diagnosis.

Turning back to FIG. 2A, the controller 180 may control overall operation of the ultrasonic apparatus. For example, the controller 180 may control the image processing unit 170 or the display 160 based on control instructions input to the input unit 150.

The controller 180 may also analyze the area of interest matched or correlated by the image processing unit 170 to determine whether a biopsy is required for the subject. Specifically, the controller 180 may determine whether a biopsy is required for the subject by comparing characteristic information of the matched area of interest with reference characteristic information determined in advance.

Here, the characteristic information may refer to information based on which determination of whether a biopsy is required is made. Specifically, the characteristic information of an area of interest may include at least one of the size, shape, texture, spiculation form, and brightness per unit area of the area of interest.

The reference characteristic information may refer to a value to be compared with the characteristic information to determine whether a biopsy is required. The reference characteristic information may be determined based on a user input or by calculation in the ultrasonic apparatus.

In particular, the reference characteristic information may be determined based on clinical data from a sample group obtained before diagnosis of the subject. For example, characteristic information is obtained from a sample group of one hundred patients, and a maximum value, a minimum value, or an average value of the characteristic information may be determined to be the reference characteristic information.

The controller 180 may obtain a malignancy score of the area of interest by comparing the characteristic information of the area of interest with the reference characteristic information. For example, in a case that the reference characteristic information corresponds to average characteristic information obtained from a sample group that requires a biopsy, as the characteristic information in the area of interest is closer to the reference characteristic information, a greater malignancy score may be obtained.

After obtaining the malignancy score in the area of interest, the controller 180 may obtain at least one of the true positive rate and the false positive rate of the area of interest.

The true positive rate of the area of interest may refer to a probability that the controller 180 has determined that a biopsy is required for the area that requires the biopsy. As the true positive rate increases, the reliability of the determination that the biopsy is required may increase.

The false positive rate of the area of interest may refer to a probability that the controller 180 determines that a biopsy is required for the area of interest that does not require the biopsy. As the false positive rate increases, risks associated with performing the biopsy based on the determination that the biopsy is required may increase.

To obtain at least one of the true positive rate and the false positive rate of the area of interest, the controller 180 may refer to a subject parameter. The subject parameter may refer to information regarding the subject itself associated with the determination as to whether the biopsy is required. Specifically, the subject parameter may be a numerical value of at least one of tissue density, Body Mass Index (BMI), the number of biopsies, information about family history of illness, and a particular gene (e.g., BRCA1 or BRCA2) of the subject.

The controller 180 may obtain the true positive rate $P_{test}$(Conf) of the area of interest according to the following equation 1:

$$P_{test}(Conf \mid S_M = s_m, S_U = s_u, C) = \frac{\exp(\alpha_0 + \alpha_1 s_m + \alpha_2 s_u + \alpha_3 c_1 + \ldots + \alpha_{N+2} c_N)}{1 + \exp(\alpha_0 + \alpha_1 s_m + \alpha_2 s_u + \alpha_3 c_1 + \ldots + \alpha_{N+2} c_N)} \quad (1)$$

where, $\alpha_i$ (i=0, 1, . . . , N+2) is a regression coefficient calculated from reweighted least square algorithm, $S_M$ is a malignancy score obtained based on the area of interest in the X-ray image, $S_U$ is a malignancy score obtained based on the area of interest in the ultrasound image, and C={$C_1$, $C_2$, . . . , $C_N$} is a set of subject parameters (e.g., {the number of biopsies=4, age=68}).

The true positive rate $P_{test}$(Conf) has a probability value ranging from 0 to 1.

The controller 180 may obtain the false positive rate $P_{test}$(Risk) of the area of interest according to the following equation 2:

$$P_{test}(\text{Risk} \mid S_M = s_m, S_U = s_u, C) = \frac{\exp(\beta_0 + \beta_1 s_m + \beta_2 s_u + \beta_3 c_1 + \ldots + \beta_{N+2} c_N)}{1 + \exp(\beta_0 + \beta_1 s_m + \beta_2 s_u + \beta_3 c_1 + \ldots + \beta_{N+2} c_N)} \quad (2)$$

where, $\beta_i$ (i=0, 1, . . . , N+2) is a regression coefficient calculated from reweighted least square algorithm, $S_M$ is a malignancy score obtained based on the area of interest in the X-ray image, $S_U$ is a malignancy score obtained based on the area of interest in the ultrasound image, and $C=\{C_1, C_2, \ldots, C_N\}$ is a set of subject parameters (e.g., {the number of biopsies=4, age=68}).

The false positive rate $P_{test}$(Risk) has a probability value ranging from 0 to 1.

Based on at least one of the true positive rate and the false positive rate obtained as described above, the controller 180 may determine whether the biopsy is required in the area of interest.

Specifically, the controller 180 may determine that the biopsy is required for the area of interest if the true positive rate $P_{test}$(Conf) satisfies the following equations 3 and 4.

$$P_{test}(\text{Conf}) > \overline{P}_{train}(\text{Conf}) \quad (3)$$

$$\overline{P}_{train}(\text{Conf}) = \frac{1}{M} \sum_{i=1}^{M} P_{train}^{(i)}(\text{Conf}) \quad (4)$$

where, $\overline{P}_{train}$(Conf) represents a reference true positive rate, and $P_{train}^{(i)}$(Conf) represents the true positive rate for the $i^{th}$ sample in the sample group consisting of M true positive samples.

The sample group of M true positive samples may be included in a sample group with which to determine the reference characteristic information. Accordingly, the reference characteristic information may be determined based on characteristic information of the sample group, and the controller 180 may determine a reference true positive rate based on the reference characteristic information.

As such, the controller 180 may determine that the biopsy is required if the true positive rate in the area of interest obtained from the equation 3 is higher than the reference true positive rate.

The controller 180 may also determine that the biopsy is required for the area of interest if the false positive rate $P_{test}$(Risk) satisfies the equations 5 and 6.

$$P_{test}(\text{Risk}) < \overline{P}_{train}(\text{Risk}) \quad (5)$$

$$\overline{P}_{train}(\text{Risk}) = \frac{1}{K} \sum_{i=1}^{K} P_{train}^{(i)}(\text{Risk}) \quad (6)$$

where, $\overline{P}_{train}$(Risk) represents a reference false positive rate, and $P_{train}^{(i)}$(Risk) represents the false positive rate for the $i^{th}$ sample in the sample group consisting of K false positive samples.

The sample group of K false positive samples may be included in a sample group with which to determine the reference characteristic information. Accordingly, the reference characteristic information may be determined based on characteristic information of the sample group, and the controller 180 may determine a reference false positive rate based on the reference characteristic information.

As such, the controller 180 may determine that the biopsy is required if the false positive rate in the area of interest obtained from the equation 5 is lower than the reference false positive rate.

Alternatively, the controller 180 may determine that the biopsy is required if the true positive rate in the area of interest is higher than the reference true positive rate and the false positive rate in the area of interest is lower than the reference false positive rate.

Meanwhile, the controller 180 may update the reference characteristic information as well, based on whether the biopsy is required. As described above, since the reference characteristic information is empirically determined using the characteristic information of a predetermined sample group, characteristic information of a current area of interest subject to determination of whether the biopsy is required may also be a sample for determining the reference characteristic information. Thus, the controller 180 may update the reference characteristic information based on the characteristic information of the area of interest subject to determination of whether the biopsy is required.

Turning back to FIG. 2A, the display 160 may indicate whether the biopsy is required according to the determination result from the controller 180.

Figure 5A:
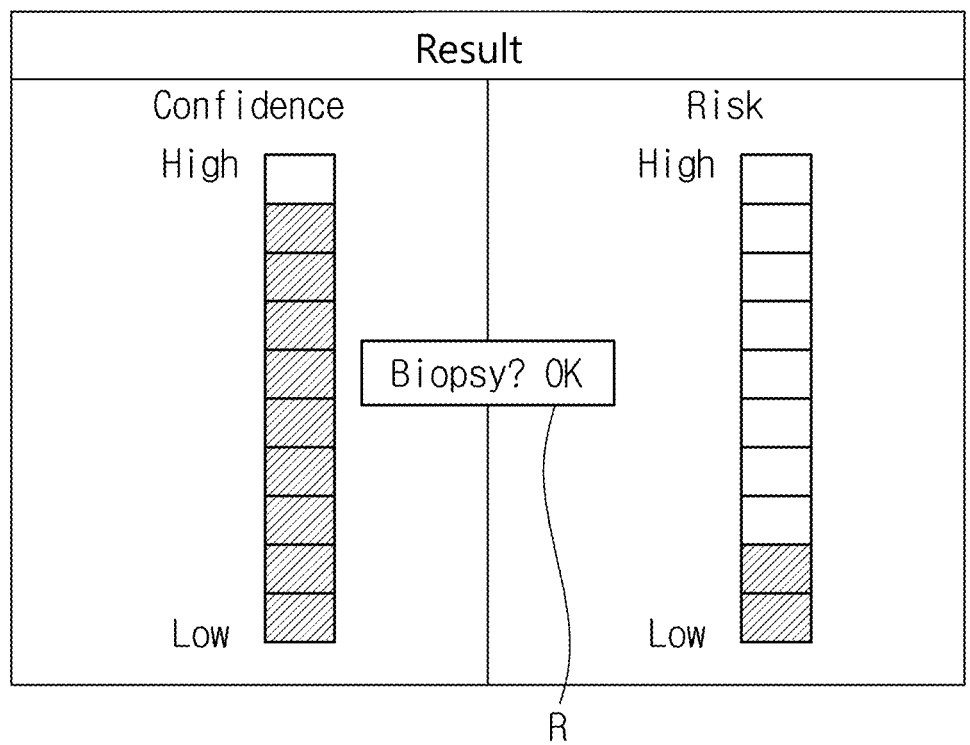
FIGS. 5A and 5B show a various indications displayed on a display of an ultrasonic apparatus, according to an embodiment of the present disclosure.
Figure 5B:
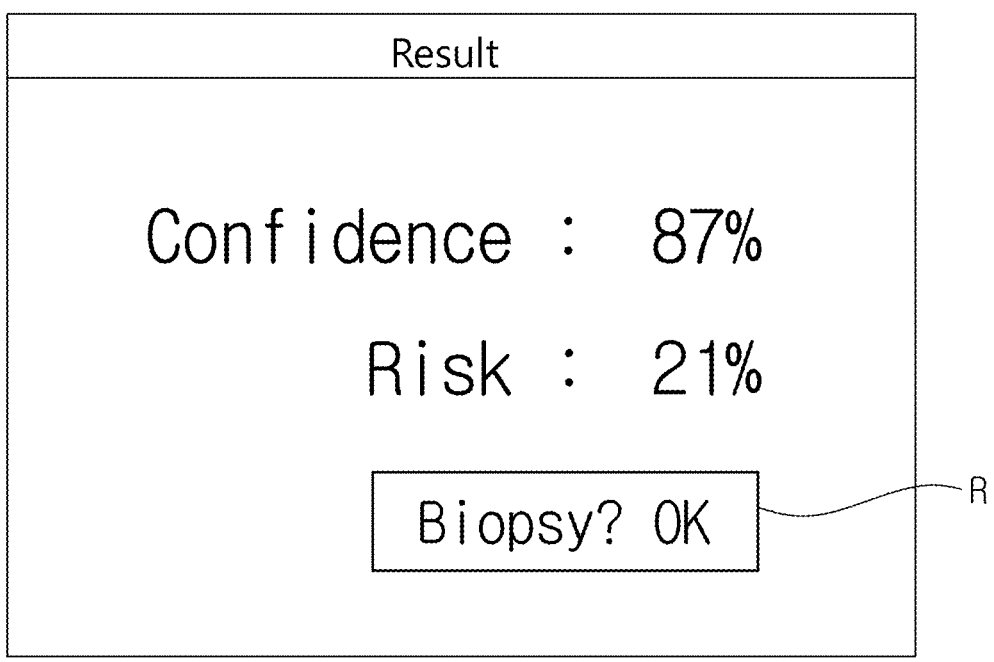

FIGS. 5A and 5B show various indications displayed on a display of an ultrasonic apparatus, according to an embodiment of the present disclosure.

The display 160 may indicate the true positive rate and the false positive rate obtained from the controller 180. For example, the display 160 may indicate the true positive rate and false positive rate by quantifying (or charting) them as a confidence degree and risk degree, respectively.

FIG. 5A shows an occasion where the display 160 indicates the confidence degree (referring to the true positive rate) and risk degree (referring to the false positive rate) in bar-like forms, and FIG. 5B shows an occasion where the display 160 indicates the confidence and risk degrees in percentage terms.

The display 160 may indicate the determination of whether the biopsy is required, which has been made by the controller 180, together with the true and false positive rates. It may be seen from FIGS. 5A and 5B that the display 160 indicates determination R of whether the biopsy is required with the confidence and risk degrees.

Moreover, the display 160 may display diagnosis guidelines G based on the determination of whether the biopsy is required made by the controller 180.

Figure 6A:
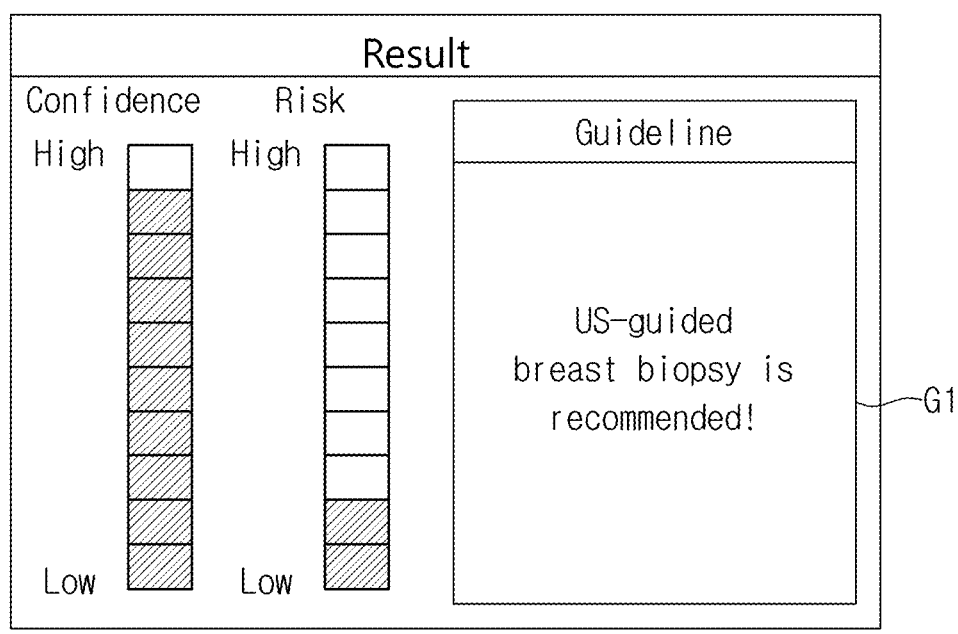
FIGS. 6A and 6B show diagnosis guidelines displayed on a display of an ultrasonic apparatus, according to an embodiment of the present disclosure.
Figure 6B:
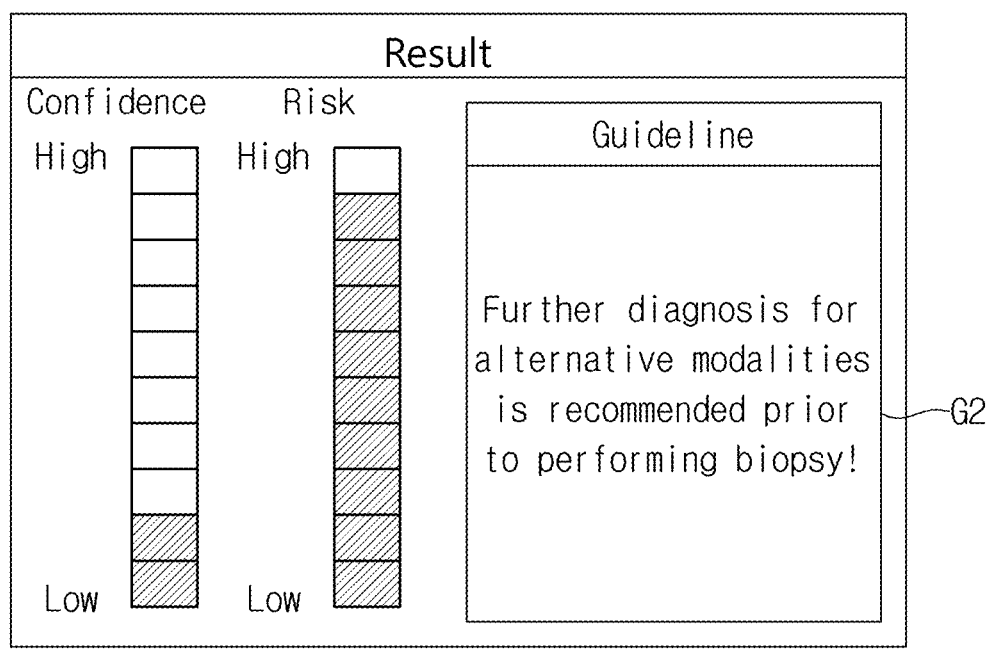

FIGS. 6A and 6B show diagnosis guidelines displayed on a display of an ultrasonic apparatus, according to an embodiment of the present disclosure.

The display 160 may display diagnosis guidelines G based on the determination of whether the biopsy is required made by the controller 180. Specifically, if the controller 180 determines that the biopsy is required for the area of interest, the display 160 may display a biopsy recommendation screen $G_1$. Otherwise, if the controller 180 determines that the biopsy is not required for the area of interest, the display 160 may display an alternative diagnosis method recommendation screen $G_2$.

FIG. 6A shows a screen displayed by the display 160 in an occasion where the controller 180 determines that the biopsy is required for the area of interest. Referring to FIG. 6A, the display 160 may display the biopsy recommendation screen $G_1$ while displaying the true and false positive rates in the bar form as shown in FIG. 5A.

The user might proceed with the biopsy for the area of interest by checking it out from or based on the display 160.

FIG. 6B shows a screen displayed by the display 160 in an occasion where the controller 180 determines that the biopsy is not required for the area of interest. Referring to FIG. 6B, the display 160 may display an alternative diagnosis method recommendation screen $G_2$ while displaying the true and false positive rates in the bar form. The alternative diagnosis method may include any other diagnosis methods except for the biopsy.

The user may perform any diagnosis method other than the biopsy for the area of interest by checking it out from or based on the display 160.

It has thus far been described that the ultrasonic apparatus directly communicates with the external X-ray apparatus 300 and the external storage unit, as shown in FIG. 2A. However, it may also possible for the ultrasonic apparatus to be connected to the network 500 and communicate with external devices over the network 500.

FIG. 2B shows an occasion where the ultrasonic apparatus is connected to the network 500 and exchanges information with external devices over the network 500. Unlike the occasion of FIG. 2A where the image processing unit 170 receives an X-ray image directly from the X-ray apparatus 300, the image processing unit 170 of FIG. 2B may receive an X-ray image from the X-ray apparatus 300 over the network 500. Moreover, the controller 180 may also receive the reference characteristic information from the storage unit 400 over the network 500.

A method for controlling the ultrasonic apparatus will now be described with reference to FIGS. 7 to 11.

Figure 7:
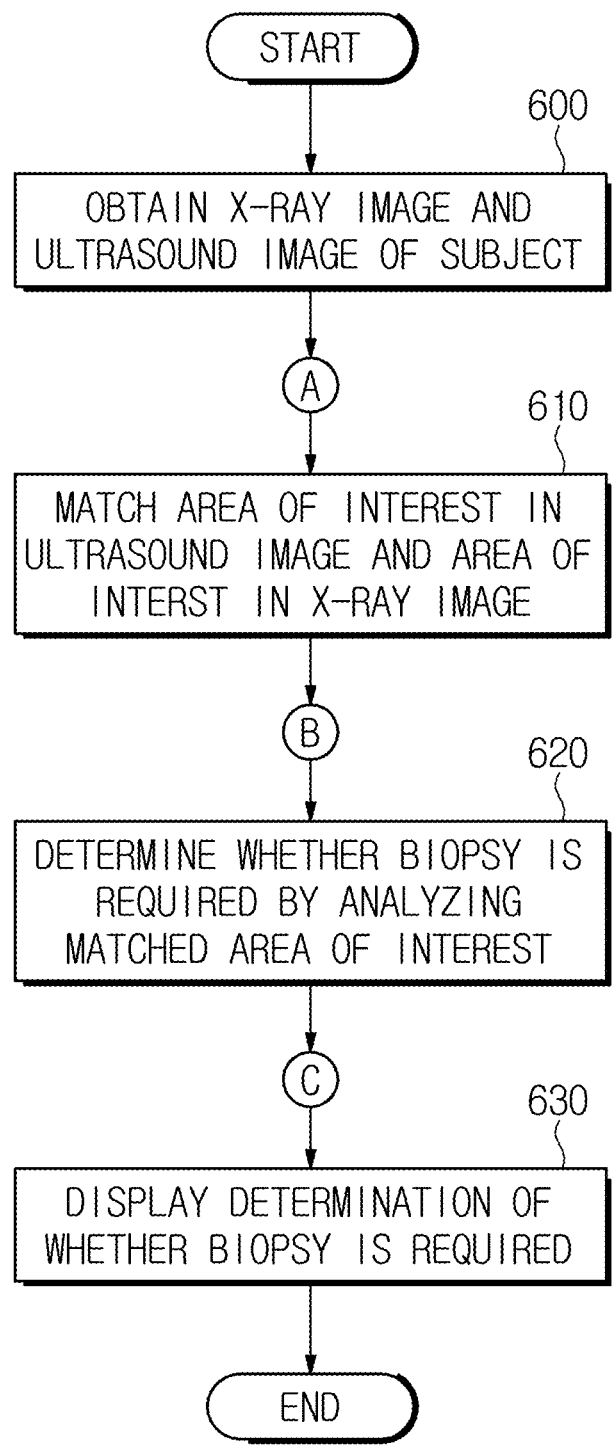
FIG. 7 is a flowchart illustrating a method for controlling an ultrasonic apparatus, according to an embodiment of the present disclosure.

FIG. 7 is a flowchart illustrating a method for controlling an ultrasonic apparatus, according to an embodiment of the present disclosure.

First, an ultrasound image and X-ray image of a subject may be obtained in operation 600. In this case, a determination of whether a biopsy is required is made based on both the X-ray and ultrasound images, thus increasing reliability of the determination.

There are many ways to obtain the ultrasound and X-ray images. In the following, various embodiments of obtaining the ultrasound and X-ray images (operation 600) will be described in connection with FIGS. 8A and 8B.

Figure 8A:
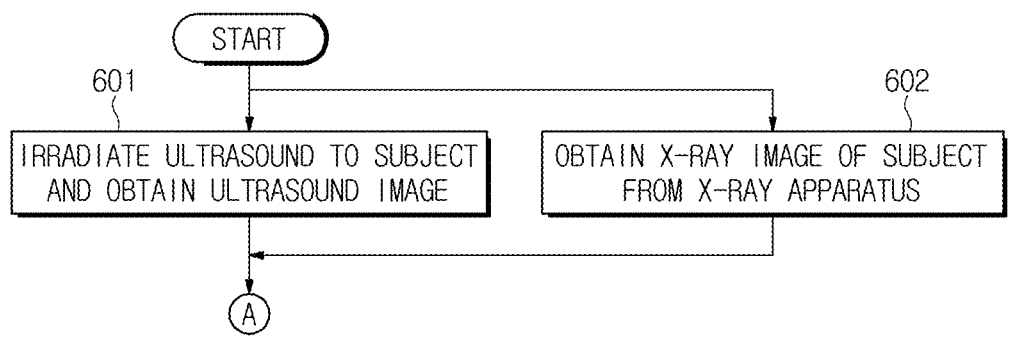
FIGS. 8A and 8B are flowcharts illustrating a method for controlling an ultrasonic apparatus to obtain ultrasound and X-ray images, according to various embodiments of the present disclosure.
Figure 8B:
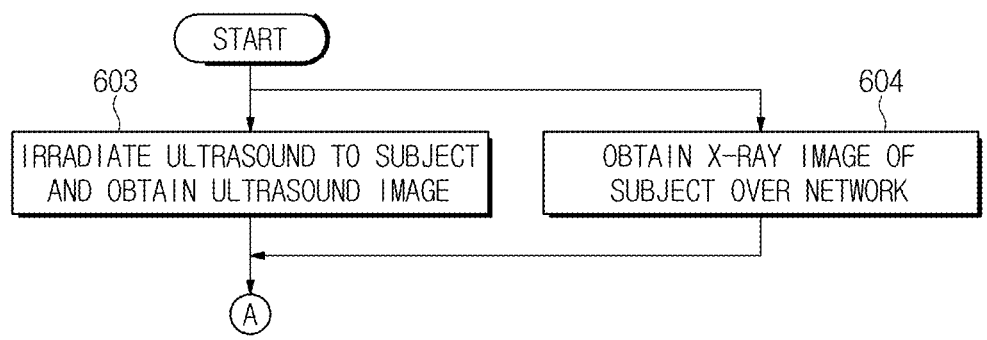

FIGS. 8A and 8B are flowcharts illustrating a method for controlling an ultrasonic apparatus to obtain ultrasound and X-ray images, according to various embodiments of the present disclosure.

Referring to FIG. 8A, the ultrasonic apparatus may obtain an ultrasound image by irradiating ultrasound into the subject, in operation 601. Specifically, the ultrasonic apparatus may irradiate ultrasound into the subject, receive echo ultrasound reflected from the subject, and convert the echo ultrasound into an ultrasound image.

With this, the ultrasonic apparatus may directly receive an X-ray image of the subject from the external X-ray apparatus 300, in operation 602.

Unlike the occasion of FIG. 8A, the ultrasonic apparatus and the X-ray apparatus 300 may not be directly connected to each other. Referring to FIG. 8B, the ultrasonic apparatus may receive the X-ray image through the network, in operation 604. For this, the ultrasonic apparatus and the X-ray apparatus 300 need to be connected to the same network.

Unlike the occasions of FIGS. 8A and 8B, it may also possible for the ultrasonic apparatus to obtain the ultrasound image from an external device or through the network.

Turning back to FIG. 7, after the ultrasound and X-ray images are obtained, areas of interest in the ultrasound and X-ray images may be matched to each other, in operation 610.

The area of interest may refer to an area for which it is determined whether a biopsy is required and be defined to be an area determined in the ultrasound image or X-ray image and a corresponding area of the subject.

There are many ways to match the areas of interest. In the following, various embodiments of operation 610 of matching or correlating the areas of interest will be described in connection with FIGS. 9A to 9C.

Figure 9A:
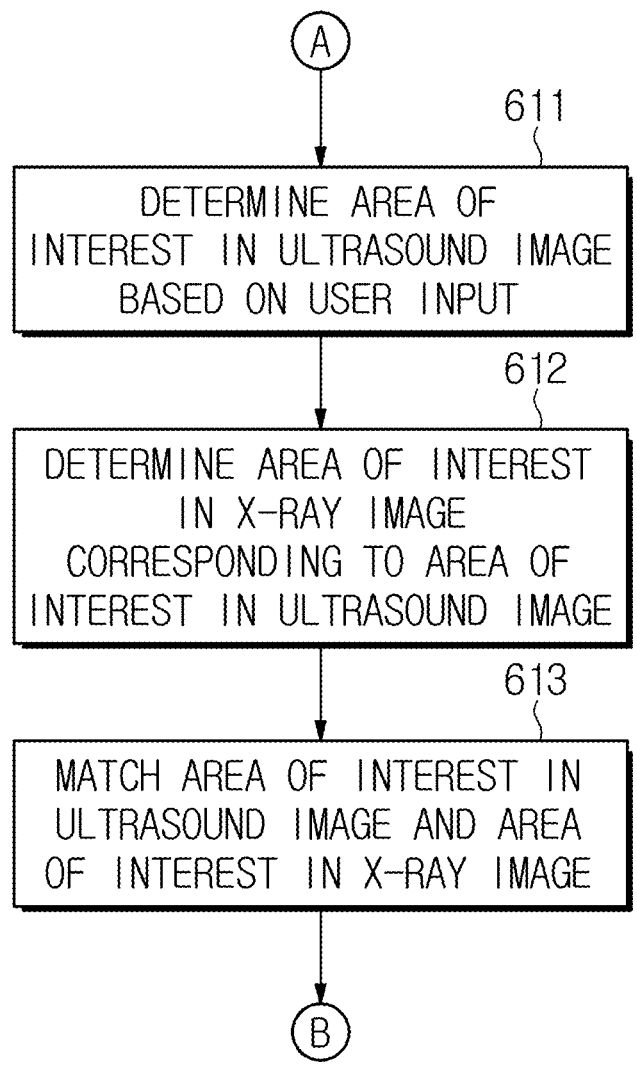
Figure 9C:
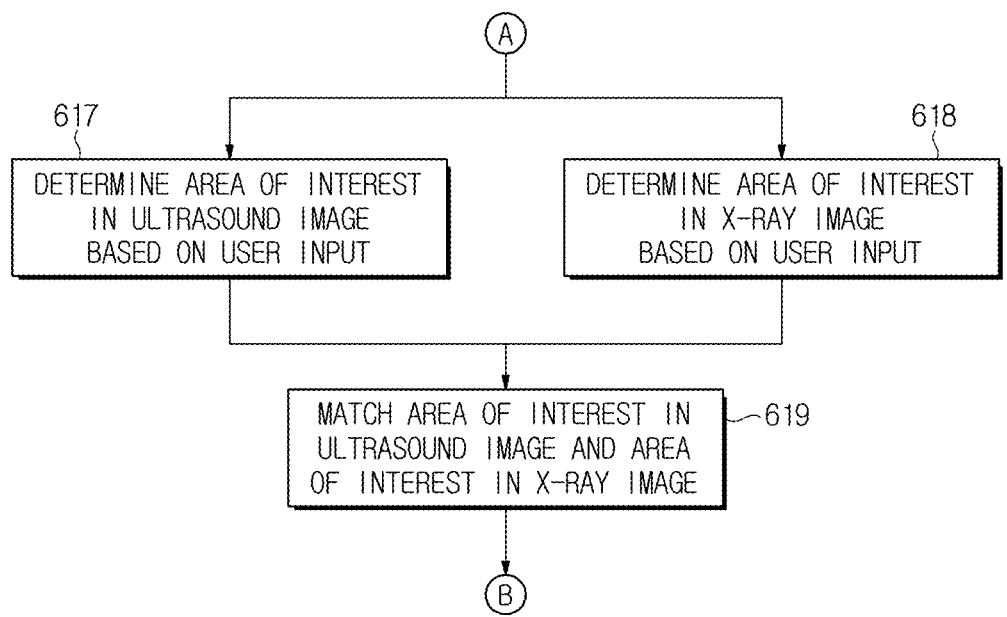

FIGS. 9A to 9C are flowcharts illustrating a method for controlling an ultrasonic apparatus to match areas of interest, according to various embodiments of the present disclosure.

Referring to FIG. 9A, an area of interest in the ultrasound image may be determined in response to a user input, in operation 611.

Upon determination or designation of the area of interest in the ultrasound image, a corresponding area of interest in the X-ray image may be determined, in operation 612. Here, the area of interest in the X-ray image corresponding to the area of interest in the ultrasound image may refer to an area in the X-ray image that displays a location in the subject of a part displayed in the area of interest in the ultrasound image.

Upon determination of the respective areas of interest in the ultrasound image and the X-ray image, the areas of interest may be matched together or correlated, in operation 613. Here, the matching may refer to corresponding or correlating an area of interest in the ultrasound image and an area of interest in the X-ray image using coordinates of the coordinate system.

Alternatively, referring to FIG. 9B, an area of interest in the X-ray image may be determined first in response to a user input, in operation 614.

Upon determination of the area of interest in the X-ray image, a corresponding area of interest in the ultrasound image may be determined, in operation 615.

Finally, the areas of interest may be matched or correlated together, in operation 616.

Alternatively, referring to FIG. 9C, both areas of interest in the ultrasound image and X-ray image may be determined in response to a user input, in operations 617 and 618. The areas of interest may then be matched together, in operation 619.

Turning back to FIG. 7, the matched area of interest may be analyzed to determine whether a biopsy is required, in operation 620. For this, the true and false positive rates of the area of interest may be used. In the following, operation 620 of determining whether a biopsy is required using the true and false positive rates will be described in more detail in connection with FIG. 10.

Figure 10:
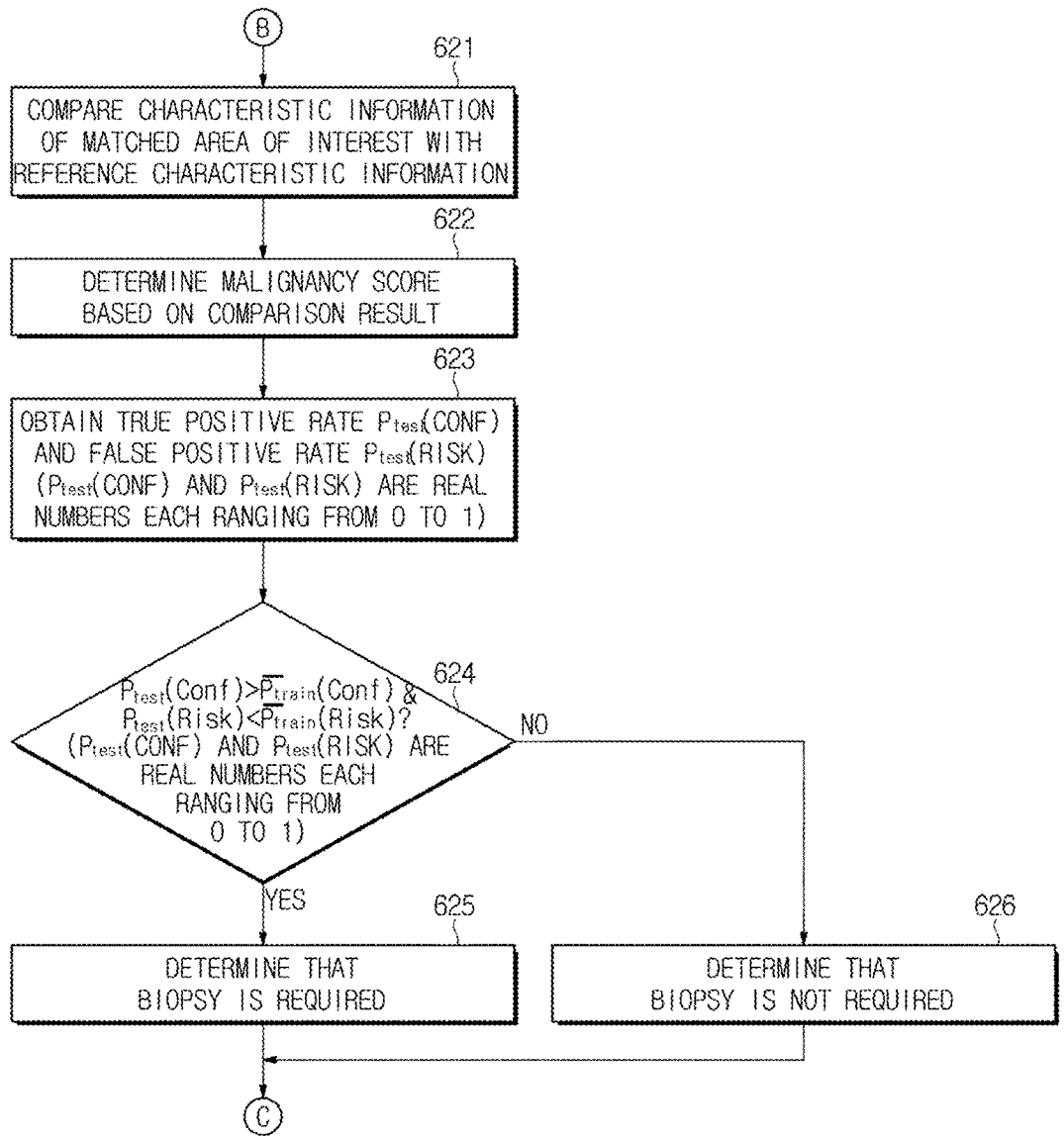
FIG. 10 is a flowchart illustrating a method for controlling an ultrasonic apparatus to determine whether a biopsy is required, according to an embodiment of the present disclosure.

FIG. 10 is a flowchart illustrating a method for controlling an ultrasonic apparatus to determine whether a biopsy is required, according to an embodiment of the present disclosure.

First, the characteristic information of the matched area of interest may be compared with the reference characteristic information, in operation 621. Here, the characteristic information may refer to information based on which determination of whether a biopsy is required is made. Specifically, the characteristic information of an area of interest may include at least one of the size, shape, texture, spiculation form, and brightness per unit area of the matched area of interest.

The reference characteristic information may refer to a value to be compared with the characteristic information to determine whether a biopsy is required.

After the comparison, a malignancy score may be determined based on the comparison result, in operation 622. The malignancy score may increase as the characteristic information of the area of interest is similar to the reference characteristic information.

Based on the malignancy score and the subject parameter, the true positive rate $P_{test}$(Conf) and the false positive rate $P_{test}$(Risk) may be obtained, in operation 623. The true positive rate Ptest(Conf) of the area of interest may refer to a probability that the controller 180 determines or has determined that a biopsy is required for the area that requires the biopsy. The false positive rate $P_{test}$(Risk) of the area of interest may refer to a probability that the controller 180 determines that a biopsy is required for the area that does not require the biopsy.

To obtain both the true positive rate $P_{test}$(Conf) and the false positive rate $P_{test}$(Risk), a subject parameter is used together with the characteristic information of the area of interest. The subject parameter may refer to information regarding the subject itself associated in the determination of whether the biopsy is required.

The true positive rate $P_{test}$(Conf) may be obtained by the equation 1. The false positive rate $P_{test}$(Risk) may be obtained by the equation 2.

It is determined if or whether the true positive rate $P_{test}$(Conf) of the area of interest is greater than the reference true positive rate, in operation 624. Since the true positive rate is related to reliability of determining whether the biopsy is required or biopsy risks, the biopsy may be required if the true positive rate is greater than the predetermined reference true positive rate.

Furthermore, it is determined if the false positive rate $P_{test}$(Risk) is less than the reference false positive rate, in operation 624. Since the false positive rate is related to risks of determining whether the biopsy is required, the biopsy may be required if the false positive rate is less than the predetermined reference false positive rate.

If both conditions described above are met, it is determined that the biopsy is required, in operation 625.

Otherwise, if one of the conditions described above is not met, it is determined that the biopsy is not required, in operation 626.

However, the aforementioned is merely an example of a method for determining whether the biopsy is required, and it may be determined that the biopsy is required if at least one of the two conditions is met in another example.

Turning back to FIG. 7, the determination of whether the biopsy is required may be displayed, in operation 630. The operation 630 of displaying whether the biopsy is required will now be described in more detail in connection with FIG. 11.

Figure 11:
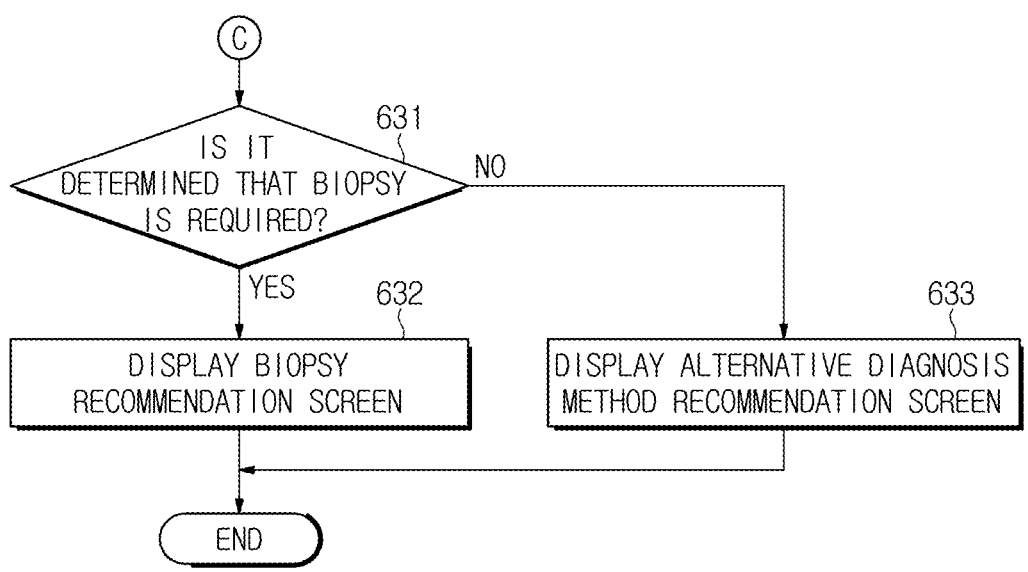
FIG. 11 is a flowchart illustrating a method for controlling an ultrasonic apparatus to indicate whether a biopsy is required, according to an embodiment of the present disclosure.

FIG. 11 is a flowchart illustrating a method for controlling an ultrasonic apparatus to indicate or display whether a biopsy is required, according to an embodiment of the present disclosure.

First, it is determined if it has been determined that the biopsy is required, in operation 631.

If it has been determined that the biopsy is required, a screen for recommending to perform the biopsy may be displayed, in operation 632.

Otherwise, if it has been determined that the biopsy is not required, a screen for recommending an alternative diagnosis method other than the biopsy may be displayed, in operation 633.

By doing the operation, the user may be provided with an indication of whether a biopsy is required and corresponding guidelines, thereby performing more efficient diagnosis.

In accordance with an aspect of the present disclosure, using both X-ray and ultrasound images may increase accuracy in determining whether a biopsy is required.

In accordance with another aspect of the present disclosure, an environment for a user to easily perform ultrasonic diagnosis may be provided by displaying an indication of whether a biopsy is required together with corresponding diagnosis guidelines.

Several embodiments have been described, but a person of ordinary skill in the art will understand and appreciate that various modifications can be made without departing the scope of the present disclosure. Thus, it will be apparent to those ordinary skilled in the art that the disclosure is not limited to the embodiments described, which have been provided only for illustrative purposes.

What is claimed is:

1. A method for controlling an ultrasonic apparatus, the method comprising:
matching an ultrasound area of interest in an ultrasound image of a subject and an X-ray area of interest in a X-ray image of the subject to produce a matching area of interest;
obtaining an X-ray malignancy score of the matching area of interest by comparing characteristic information of the matching area of interest in the X-ray image with predetermined reference characteristic information;
obtaining an ultrasound malignancy score of the matching area of interest by comparing characteristic information of the matching area of interest in the ultrasound image with predetermined reference characteristic information;
obtaining a true positive rate and a false positive rate of the matching area of interest based on the X-ray malignancy score, the ultrasound malignancy score, and a set of subject parameters;
determining whether a biopsy is required for the subject based on the true positive rate and the false positive rate of the matching area of interest; and
displaying the determination of whether the biopsy is required,
wherein the predetermined reference characteristic information comprises at least one of a size, shape, texture, spiculation form, and brightness per unit area of the matching area of interest, and
wherein the set of subject parameters comprises at least one of tissue density, Body Mass Index (BMI), the number of biopsies, information about family history of illness, and a particular gene of the subject.

2. The method of claim 1, further comprising: updating the reference characteristic information based on the determination of whether the biopsy is required.

3. The method of claim 1, wherein determining whether a biopsy is required comprises determining whether the biopsy is required for the subject by comparing at least one of the obtained true positive rate and false positive rate with at least one of a predetermined reference true positive rate and reference false positive rate, respectively.

4. The method of claim 3, wherein the determining whether a biopsy is required comprises at least one of:
   determining that the biopsy is required when the true positive rate in the area of interest is higher than the predetermined reference true positive rate, and
   determine that the biopsy is required when the false positive rate in the area of interest is lower than the predetermined reference false positive rate.

5. The method of claim 1, wherein the displaying the determination of whether the biopsy is required comprises displaying diagnosis guidelines based on the determination of whether the biopsy is required.

6. The method of claim 5, wherein displaying diagnosis guidelines comprises:
   displaying a biopsy recommendation screen if it is determined that the biopsy is required, and
   displaying an alternative diagnosis method recommendation screen if it is determined that the biopsy is not required.

7. The method of claim 1, further comprising:
   determining an ultrasound area of interest in the ultrasound image based on a user input; and
   determining an X-ray area of interest in an X-ray image based on the area of interest in the ultrasound image.

8. The method of claim 1, wherein the displaying the determination of whether the biopsy is required includes indicating the true positive rate and false positive rate by illustrating the true positive rate and false positive rate as a confidence degree and risk degree, respectively.

* * * * *